(12) United States Patent
Taketomi et al.

(10) Patent No.: US 6,197,996 B1
(45) Date of Patent: Mar. 6, 2001

(54) PROCESS FOR PREPARING OPTICALLY ACTIVE CARNITINE ESTER

(75) Inventors: Takanao Taketomi, Chiba; Toshiaki Sakaguchi; Hidenori Kumobayashi, both of Kanagawa, all of (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 08/139,861

(22) Filed: Oct. 22, 1993

Related U.S. Application Data

(63) Continuation of application No. 07/455,023, filed on Dec. 22, 1989.

(30) Foreign Application Priority Data

Dec. 22, 1988 (JP) .................................................. 63-324651

(51) Int. Cl.[7] .................................................. C07C 229/00
(52) U.S. Cl. .......................................................... 560/170
(58) Field of Search ............................................. 560/170

(56) References Cited

U.S. PATENT DOCUMENTS

| 4,021,480 | * | 5/1977 | Tenud | 560/170 |
| 4,600,794 | * | 7/1986 | Tinti | 560/170 |
| 4,691,037 | * | 9/1987 | Yoshikawa et al. | 556/23 |
| 4,739,085 | * | 4/1988 | Takaya et al. | 556/23 |
| 4,916,252 | * | 4/1990 | Sayo et al. | 560/170 |

FOREIGN PATENT DOCUMENTS

| 0169614 | 1/1986 | (EP) | 560/170 |
| 0339764 | 11/1989 | (EP) | 560/170 |

OTHER PUBLICATIONS

Kitamura, M. et al, *Tetrahedron Letters*, 29:13 1555–1556 (1988).
Noyori, R. et al, *Journal of American Chemical Society*, vol. 109, 5856–5858 (1987).

\* cited by examiner

*Primary Examiner*—James H. Reamer
(74) *Attorney, Agent, or Firm*—Sughrue, Mion, Zinn, Macpeak & Seas, PLLC

(57) ABSTRACT

A process for preparing an optically active carnitine ester represented by formula (I):

$$\left( (CH_3)_3N^+ \underset{}{\overset{OH}{\smile}} \underset{OR}{\overset{O}{\smile}} \right) X^-  \quad (I)$$

wherein R represents a lower alkyl group; and X represents a halogen atom, is disclosed, comprises asymmetrically hydrogenating a γ-trimethylammonium-3-oxobutanoic ester halide represented by formula (II):

$$\left( (CH_3)_3N^+ \underset{}{\overset{O}{\smile}} \underset{OR}{\overset{O}{\smile}} \right) X^-  \quad (II)$$

wherein R and X are as defined above, in the presence of a ruthenium-optically active phosphine complex as a catalyst. An optically active carnitine ester of any desired isomerism can be obtained through simple operation in high yield at high optical purity. The substrate used is easily available.

24 Claims, No Drawings

PROCESS FOR PREPARING OPTICALLY ACTIVE CARNITINE ESTER

This is a Continuation of application Ser. No. 07/455,023 filed Dec. 22, 1989.

FIELD OF THE INVENTION

This invention relates to a process for preparing an optically active carnitine ester which is an intermediate for obtaining medicinally important optically active carnitine. More particularly, it relates to a process for preparing an optically active carnitine ester by asymmetric hydrogenation of a γ-trimethylammonium-3-oxobutanoic ester halide in the presence of a ruthenium-optically active phosphine complex as a catalyst.

BACKGROUND OF THE INVENTION

L-Carnitine is present in a living body and functions to carry activated long-chain free fatty acids through the mitochondrial inner membrane. Acyl-CoA derivatives are allowed to enter into the mitochondrial matrix through the mitochondrial inner membrane only in the form of their ester with L-carnitine. Such a carrier function of L-carnitine is exerted in derivering the activated long-chain fatty acids from the site of their biosynthesis. The carnitine found in the living body is exclusively levorotatory, i.e., of L-form, while D-carnitine has never been detected in living bodies.

On the other hand, racemic carnitine has been used for years for various purposes. For example, DL-carnitine has been sold in Europe as an appetizer and also reported to have an effect of promoting physical development of children as described in Borniche et al., *Olinioa Chemica Acta*, Vol. 5, pp. 171 to 176 (1960). However, in recent years, an importance of using only L-carnitine for therapeutic purposes has been increasing. That is, D-carnitine has turned out to antagonize against carnitine acyltransferase, e.g., carnitine acetyl transferase (CAT) and carnitine palmitoyl transferase (PTC). It has also been elucidated recently that D-carnitine causes depletion of L-carnitine in cardiac tissues. Accordingly, it is essential that cases under treatment for cardiac diseases or for reduction of blood fat should receive only L-carnitine. L-carnitine has thus been recognized as an important medicine.

Known techniques for preparing an optically active carnitine ester and carnitine include (i) optical resolution of a racemate, (ii) biochemical reduction of the corresponding keto ester, and (iii) synthesis using other optically active substances as a starting material or an intermediate.

Examples of the technique (i) include a process in which DL-carnitine amide hydrochloride is subjected to an ion exchange treatment and then resolved using D-camphoric acid as disclosed in JP-A-55-13299 (the term "JP-A" as used herein means an "unexamined published Japanese patent application") and a process in which DL-carnitine nitrile is resolved using L-camphor-10-sulfonic acid as disclosed in JP-B-40-3891 (the term "JP-B" as used herein means an "examined published Japanese patent application"). Examples of the technique (ii) include a process in which a γ-halo-acetoacetic ester is converted to an optically active γ-halo-β-hydroxybutyric ester by microbial fermentation and then quaternarized with trimethylamine as disclosed in JP-A-59-118093 and a process in which γ-azidoacetoacetic ester is reduced with a microorganism to obtain an optically active γ-azido-β-hydroxybutyric ester. Examples of the technique (iii) include a process using D-mannitol as disclosed in JP-A-57-165352 and a process using (S)-chloromethyloxirane as disclosed in JP-A-62-212382.

However, the processes (i) utilizing resolution of a racemate as a carnitine precursor require a resolving agent in an amount equimolar to the substrate. Also, the highest possible yield of the desired product, attained if the reaction ideally proceeds, is 50%. Namely, the undesired enantiomer is useless or must be racemized for re-use. The processes (ii) utilizing microbial asymmetric reduction are disadvantageous in that the usable substrate is limited, the production efficiency is low in many cases, and isolation of the product from the reaction solution involves complicated procedures. The processes (iii) using a naturally-occuring optically active substance as a starting material have disadvantages, such as requirement of long reaction steps.

SUMMARY OF THE INVENTION

As a result of extensive investigations with the purpose of settling the above-described problems, the inventors have found that a carnitine ester having high optical purity can be obtained in good yield by quaternarizing a γ-haloacetacetic ester with trimethylamine followed by asymmetric hydrogenation in the presence of a rhuthenium-optically active phosphine complex as a catalyst.

The present invention relates to a process for preparing an optically active carnitine ester represented by formula (I):

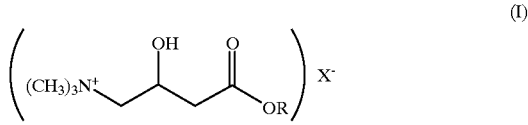

wherein R represents a lower alkyl group; and X represents a halogen atom,
which comprises asymmetrically hydrogenating a γ-trimethylammonium-3-oxobutanoic ester halide represented by formula (II):

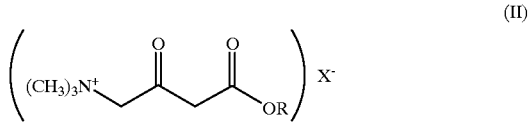

wherein R and X are as defined above,
in the presence of a ruthenium-optically active phosphine complex as a catalyst.

DETAILED DESCRIPTION OF THE INVENTION

The compound represented by formula (II) which can be used in the present invention as a starting material can easily be synthesized by, for example, the process described in JP-A-51-63123.

In formula (II), the lower alkyl group as represented by R includes those containing from 1 to 4 carbon atoms, such as methyl, ethyl, butyl, n-propyl, isopropyl, isobutyl, and t-butyl groups; and the halogen atom as represented by X includes chlorine, bromine, and iodine atoms.

Examples of suitable ruthenium-optically active phosphine complexes which can be used for asymmetric hydrogenation, include those represented by formulae (III), (V), (VI), and (VII):

wherein $R^1$—BINAP represents a tertiary phosphine represented by formula (IV):

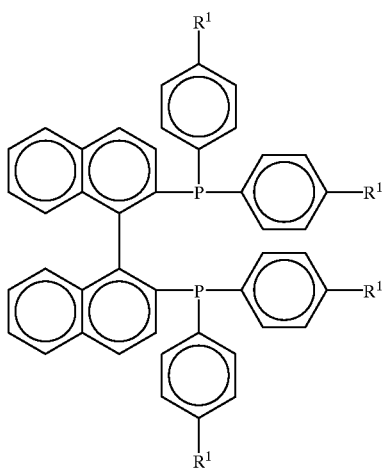
(IV)

$R^1$ represents a hydrogen atom, a methyl group or a t-butyl group; Q represents a tertiary amine; when y is 0, then x represents 2, z represents 4, and p represents 1; and when y is 1, then x represents 1, z represents 1, and p represents 0,

(V)

wherein $R^1$—BINAP is as defined above; Y represents $ClO_4$, $BF_4$ or $PF_6$; when us is 0, then v represents 1, and w represents 2; and when u is 1, then v represents 2, and w represents 1,

(VI)

wherein $R^1$—BINAP is as defined above; and $R^2$ represents a lower alkyl group (such as those containing from 1 to 4 carbon atoms) or a trifluoromethyl group, and

(VII)

wherein $R^1$—BINAP is as defined above; M represents Zn, Al, Ti or Sn; $X^1$ represents $N(C_2H_5)_3$ or $CH_3CO_2$; in the case that $X^1$ represents $N(C_2H_5)_3$, l is 2 and m is 1, and when M represents Zn, then k is 4, when M represents Al, then k is 5, and when M represents Ti or Sn, then k is 6; and in the case that $X^1$ represents $CH_3CO_2$, l is 1 and m is 2, and when M represents Zn, then k is 2, when M represents Al, then k is 3, and when M represents Ti or Sn, then k is 4.

The ruthenium-optically active phosphine complex represented by formula (III) can be obtained by the process disclosed in T. Ikariya et al., *J. Chem. Soc., Chem. Commun.*, 922–924 (1985) and JP-A-61-63690.

The complexes represented by formulae (V) and (VI) can be obtained by the processes disclosed in JP-A-63-41487 JP-A-62-265293, respectively.

The complex represented by formula (VII) can be obtained by starting with $Ru_2Cl_4(R^1$—$BINAP)_2(NEt_3)$ (wherein Et represents an ethyl group, hereinafter the same), one of the complexes of formula (III), or $Ru(R^1$—BINAP)$(OCOCH_3)_2$, or one of the complexes of formula (VI). That is, $Ru_2Cl_4(R^1$—$BINAP)_2(NEt_3)$ or $Ru(R^1$—BINAP)$(OCOCH_3)_2$ is reacted with a Lewis acid selected from zinc chloride, aluminum chloride, titanium tetrachloride, and tin tetrachloride in a solvent, e.g., methylene chloride, at a temperature of from 10 to 25° C. for a period of from 2 to 20 hours, and the solvent is removed from the reaction mixture by distillation, followed by drying to obtain the desired ruthenium-optically active phosphine complex as a solid.

Specific examples of the above-described ruthenium-optically active phosphine complexes which can be used in the present invention are shown below.

$Ru_2Cl_4(BINAP)_2(NEt_3)$
[wherein BINAP represents 2,2'-bis(diphenyl-phosphino)-1,1'-binaphthyl, i.e., the tertiary phosphine of formula (IV) wherein $R^1$ is a hydrogen atom]

$Ru_2Cl_4(T$—$BINAP)_2(NEt_3)$
[wherein T—BINAP represents 2,2'-bis(di-p-tolylphosphino)-1,1'-binaphthyl, i.e., the tertiary phosphine of formula (IV) wherein $R^1$ is a methyl group]

$Ru_1Cl_4(t$-Bu—$BINAP)_2(NEt_3)$
[wherein t-Bu—BINAP represents 2,2'-bis(di-p-butylphenylphosphino)-1,1'-binaphthyl, i.e., the tertiary phosphine of formula (IV) wherein $R^1$ is a t-butyl group]

RuHCl(BINAP)$_2$
RuHCl(T—BINAP)$_2$
RuHCl(t-Bu—BINAP)$_2$
[Ru(BINAP)](ClO$_4$)$_2$
[Ru(T—BINAP)](ClO$_4$)$_2$
[Ru(t-Bu—BINAP)](ClO$_4$)$_2$
[Ru(BINAP)](BF$_4$)$_2$
[Ru(T—BINAP)](BF$_4$)$_2$
[Ru(t-Bu—BINAP)](BF$_4$)$_2$
[Ru(BINAP)](PF$_6$)$_2$
[Ru(T—BINAP)](PF$_6$)$_2$
[Ru(BINAP)$_2$]ClO$_4$
[Ru(T—BINAP)$_2$]ClO$_4$
[Ru(BINAP)$_2$]BF$_4$
[Ru(T—BINAP)$_2$]BF$_4$
[RuH(BINAP)$_2$—PF$_6$
[RuH(T—BINAP)$_2$]PF$_6$
Ru(BINAP)(OCOCH$_3$)$_2$
Ru(BINAP)(OCOCF$_3$)$_2$
Ru(T—BINAP)(OCOCH$_3$)$_2$
Ru(BINAP)(OCO-t-Bu)$_2$ wherein t-Bu is a t-butyl group)
Ru(T—BINAP)(OCOCF$_3$)$_2$
Ru(t-Bu—BINAP)(OCOCH$_3$)$_2$
[Ru(BINAP)ZnCl$_4$]$_2$(NEt$_3$)
[Ru(BINAP)AlCl$_5$]$_2$(NEt$_3$)
[Ru(BINAP)SnCl$_6$]$_2$(NEt$_3$)
[Ru(BINAP)TiCl$_6$]$_2$(NEt$_3$)
[Ru(T—BINAP)ZnCl$_4$]$_2$(NEt$_3$)
[Ru(T—BINAP)AlCl$_5$]$_2$(NEt$_3$)
[Ru(T—BINAP)SnCl$_6$]$_2$(NEt$_3$)
[Ru(T—BINAP)TiCl$_6$]$_2$(NEt$_3$)
[Ru(BINAP)ZnCl$_2$](OCOCH$_3$)$_2$
[Ru(BINAP)AlCl$_3$](OCOCH$_3$)$_2$
[Ru(BINAP)SnCl$_4$](OCOCH$_3$)$_2$
[Ru(BINAP)TiCl$_4$](OCOCH$_3$)$_2$
[Ru(T—BINAP)ZnCl$_2$](OCOCH$_3$)$_2$

[Ru(T—BINAP)AlCl₃](OCOCH₃)₂
[Ru(T—BINAP)SnCl₄](OCOCH₃)₂
[Ru(T—BINAP)TiCl₄](OCOCH₃)₂

In carrying out the present invention, the compound of formula (II) is hydrogenated in an amphiprotic solvent, e.g., methanol, ethanol, isopropanol, and acetic acid, at a temperature of from 15 to 100° C., preferably from 35 to 70° C., at a hydrogen pressure of from 10 to 150 kg/cm², preferably from 25 to 50 kg/cm², for a period of from about 2 to 40 hours, preferably from 5 to 30 hours. The ruthenium-optically active phosphine complex is used in an amount of from 1/50 to 1/5000 mole, preferably from 1/50 to 1/1000 mole, per mole of the compound of formula (II). The solvent is used in an amount of from 2 to 10 times, preferably from 3 to 5 times, the weight of the compound of formula (II).

In this reaction, the steric configuration of the compound of formula (I) can be controlled by selecting the BINAP moiety of the catalyst. For example, S-compounds can be obtained in using (R)-(+)-BINAP moieties, and R-compounds can be obtained in using (S)-(-)-BINAP moieties.

In particular, the S-compound of formula (I) can be led to L-carnitine by hydrolysis.

After completion of the reaction, the reaction solution is concentrated under reduced pressure, and the residue is recrystallized to give the compound of formula (I). Alternatively, the residue is dissolved in water, the catalyst is removed by extraction from methylene chloride, etc., and the aqueous layer is concentrated to obtain a pure product. If desired, the catalyst may be reused for hydrogenation by removing the solvent from the extract of the catalyst and dissolving the residue in methanol or ethanol.

The present invention is now illustrated in greater detail with reference to Examples, but it should be understood that the present invention is not deemed to be limited thereto.

EXAMPLE 1

In a 500 ml-volume stainless steel-made autoclave were charged 16.3 g (72.9 mmole) of ethyl γ-trimethylammonium-3-oxobutanoate chloride, 286 mg (0.169 mmole) of Ru₂Cl₄((-)—T—BINAP)₂(NEt₃), and 100 ml of ethanol, and a hydrogenation reaction was conducted at a hydrogen pressure of 50 kg/cm² and at 25° C. for 18 hours under stirring. The ethanol was removed from the reaction mixture by distillation under reduced pressure of 20 mmHg to obtain 16.6 g of crude carnitine ethyl ester chloride.

$[\alpha]_D^{20}$:-14.7° (c=1, H₂O)
¹H NMR δ ppm: 2.28 (t, J=7.1 Hz, 3H), 2.68 (q, 2H), 3.25 (s+m, 10H), 3.50 (d, 2H), 4.23 (dq, J=2.48 Hz, 7.1 Hz, 2H), 4.7 (m, 1H)

10 grams of the resulting crude carnitine ethyl ester chloride was dissolved in 20 ml of isopropyl alcohol at 50 to 52° C. and then cooled to 5° C., followed by filtration to obtain pure carnitine ethyl ester chloride in a yield of 82%.

$[\alpha]_D^{20}$:-17.2° (c=1, H₂O)

The above-prepared crude carnitine ethyl ester chloride (10.6 g) was refluxed in 40 ml of water and 2 ml of concentrated hydrochloric acid for 2 hours, and the solution was concentrated to dryness at 60 to 65° C. under reduced pressure of 10 mmHg to obtain 9.2 g of carnitine hydrochloride (optical yield: 85.4% ee).

$[\alpha]_D^{25}$:-20.23° (c=3.59, H₂O)
¹H NMR δ ppm: 2.68 (q, 2H), 3.24 (s, 9H), 3.50 (d, 2H), 4.70 (m, 1H)

EXAMPLE 2

In 500 ml-volume stainless steel-made autoclave were charged 16.3 g (72.9 mmole) of ethyl γ-trimethylammonium-3-oxobutanoate chloride, 328 mg (0.169 mmole) of Ru₂Cl₄((-)—BINAP)₂(NEt₃), and 100 ml of ethanol, and a hydrogenation reaction was conducted at a hydrogen pressure of 25 kg/cm² and at 50° C. for 15 hours while stirring. The reaction mixture was distilled under reduced pressure of 15 mmHg to remove the ethanol to obtain 16 g of carnitine ethyl ester chloride.

$[\alpha]_D^{25}$:-14.53° (c=1, H₂O)

To the resulting carnitine ethyl ester chloride was added 50 ml of water, and subsequently 50 ml of methylene chloride was added thereto, followed by stirring. The oily layer was separated by liquid—liquid separation. To the aqueous layer was added 2 ml of concentrated hydrochloric acid, and the solution was heated at reflux for 2 hours, followed by concentration to dryness at 60 to 65° C. under reduced pressure of 1 mmHg to obtain 9.0 g of carnitine hydrochloride (optical purity: 84% ee).

$[\alpha]_D^{25}$:-18.48° (c=4.00, H₂O)

EXAMPLE 3

In 500 ml-volume stainless steel-made autoclave were charged 23.75 g (0.1 mole) of isopropyl γ-trimethylammonium-3-oxobutanoate chloride, 422 mg (0.25 mmole) of Ru₂Cl₄((-)—BINAP)₂(NEt₃), and 150 ml of isopropyl alcohol, and a hydrogenation reaction was conducted at a hydrogen pressure of 100 kg/cm² and at a temperature of 40° C. for 20 hours. The solvent was removed by distillation under reduced pressure of 10 mmHg to obtain 23.6 g of carnitine isopropyl ester chloride.

To the resulting carnitine isopropyl ester chloride was added 70 ml of water, followed by thoroughly stirring. After liquid—liquid separation, 3 ml of concentrated hydrochloric acid was added to the aqueous layer, and the solution was heated at reflux for 5 hours, followed by concentration to dryness at a liquid temperature of 60 to 65° C. under reduced pressure of 1 mmHg to obtain 16.7 g of carnitine hydrochloride (optical purity: 80% ee).

$[\alpha]_D^{25}$:-18.95° (c=1, H₂O)

EXAMPLE 4

In a 500 ml-volume stainless steel-made autoclave were charged 25.15 g (0.1 mole) of t-butyl γ-trimethylammonium-3-oxobutanoate chloride, 841 mg (1 mmole) of Ru((-)-BINAP)(OCOCH₃)₂, and 100 ml of methanol, and a hydrogenation reaction was conducted at a hydrogen pressure of 70 kg/cm² and at a temperature of 25° C. for 40 hours. The solvent was removed by distillation under reduced pressure of 20 mmHg to obtain 25.5 g of carnitine t-butyl ester chloride. The product was treated in the same manner as in Example 3 to obtain 17.7 g (90%) of L-carnitine hydrochloride (optical yield: 78.5% ee).

$[\alpha]_D^{25}$:-23.69° (c=1.05, H₂O)

EXAMPLE 5

In a 500 ml-volume stainless steel-made autoclave were charged 16.3 g (0.1 mole) of ethyl γ-trimethylammonium-3-oxobutanoate chloride, 355 mg (0.18 mmole) of [Ru((+)—BINAP)SnCl₆]₂(NEt₃), and 100 ml of ethanol, and a hydrogenation reaction was conducted at a hydrogen pressure of 100 kg/cm² and at 35° C. for 20 hours. The solvent was removed by distillation, and the residue was washed three times with 30 ml portions of methylene chloride, followed by drying at room temperature under reduced pressure of 5 mmHg for 17 hours to obtain 16 g of D-carnitine ethyl ester chloride (optical yield: 86% ee).

$[\alpha]_D^{25}$: −14.5° (c=1.0, H$_2$O)

EXAMPLES 7 TO 15

Crude carnitine ethyl ester chloride was obtained in the same manner as in Example 1, except for altering the amount of the catalyst [Ru$_2$Cl$_4$((−)—T—BINAP)$_2$(NEt$_3$)], the kind of the solvent, the hydrogen pressure, the reaction temperature, and the reaction time as indicated in Table 1 below. The optical yields of the products are shown in the Table.

TABLE 1

| | | Reaction Conditions | | | | |
|---|---|---|---|---|---|---|
| Example No. | Catalyst/ Substrate (mole/mole) | Solvent | Hydrogen Pressure (kg/cm$^2$) | Temp. (° C.) | Time (hr) | Optical Yield (% ee) |
| 7 | 1/230 | ethanol | 50 | 25 | 16 | 86.9 |
| 8 | 1/230 | ethanol | 50 | 50 | 4 | 84.6 |
| 9 | 1/230 | ethanol | 50 | 100 | 0.5 | 79.8 |
| 10 | 1/750 | ethanol | 50 | 80 | 3 | 78.0 |
| 11 | 1/750 | ethanol | 50 | 70 | 4 | 83.5 |
| 12 | 1/750 | ethanol | 50 | 60 | 5 | 85.0 |
| 13 | 1/750 | ethanol | 25 | 70 | 5 | 82.0 |
| 14 | 1/750 | ethanol | 10 | 70 | 6 | 82.0 |
| 15 | 1/230 | acetic acid | 50 | 50 | 6 | 89.8 |

As described above, the present invention provides a process for preparing an optically active carnitine ester which is an intermediate for obtaining pharmaceutically important carnitine. Using an easily available substrate and conducting asymmetrical hydrogenation in the presence of a ruthenium-optically active phosphine complex as a catalyst, the process of the present invention produces the desired compound in higher yield and at higher optical purity with high efficiency as compared with the conventional processes requiring complicated procedures and, thus, the process of the invention is of industrial advantage. Since a product of any desired isomerism can be arbitrarily obtained depending on the optical properties of the ruthenium-optically active phosphine complex used as a catalyst, it is expected to apply the present invention to a broadened range of use.

While the invention has been described in detail and with reference to specific embodiments thereof, it will be apparent to one skilled in the art that various changes and modifications can be made therein without departing from the spirit and scope thereof.

What is claimed is:
1. A process for preparing an optically active carnitine ester represented by formula (I):

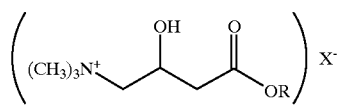

(I)

wherein R represents a lower alkyl group having two or more carbon atoms; and X represents a halogen atom,
which process consists essentially of asymmetrically hydrogenating a γ-trimethylammonium-3-oxabutanoic ester halide represented by formula (II):

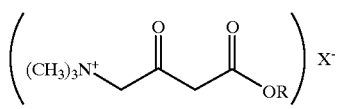

(II)

wherein R and X are as defined above,
in the presence of a ruthenium-optically active phosphine complex as a catalyst,
and then recovering the optically active carnitine ester represented by formula (I) which has been formed, wherein said ruthenium-optically active phosphine complex is selected from the group consisting of a compound represented by formula (III):

(III)

wherein R$^1$—BINAP represents a tertiary phosphine represented by formula (IV):

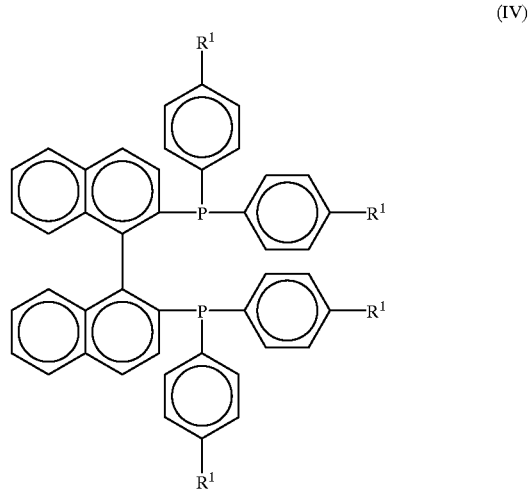

(IV)

R$^1$ represents a hydrogen atom, a methyl group or a t-butyl group;
Q represents a tertiary amine; y is 0, x represents 2, z represents 4, and p represents 1;
a compound represented by formula (VI):

(VI)

wherein R$^1$—BINAP is as defined above; and R$^2$ represents a lower alkyl group or a trifluoromethyl group; and a compound represented by formula (VII):

(VII)

wherein R$^1$—BINAP is as defined above; M represents Zn, Al, Ti or Sn; X$^1$ represents N(C$_2$H$_5$)$_3$ or CH$_3$CO$_2$; in the case that X$^1$ represents N(C$_2$H$_5$)$_3$, l is 2 and m is 1, and when M represents Zn, then k is 4, when M represents Al, then k is 5, and when M represents Ti or Sn, then k is 6; and in the case that X$^1$ represents CH$_3$CO$_2$, l is 1 and m is 2, and when M represents Zn, then k is 2, when M represents Al, then k is 3, and when M represents Ti or Sn, then k is 4.

2. A process as claimed in claim 1, wherein said ruthenium-optically active phosphine complex is used in an amount of from 1/50 to 1/5000 mole per mole of the compound of formula (II).

3. A process as claimed in claim 2, wherein said ruthenium-optically active phosphine complex is used in an amount of from 1/50 to 1/1000 mole per mole of the compound of formula (II).

4. A process as claimed in claim 1, wherein the hydrogenation is carried out at a temperature of from 15 to 100° C. and at a hydrogen pressure of from 10 to 150 kg/cm$^2$ for a period of from about 2 to 40 hours.

5. A process as claimed in claim 4, wherein the hydrogenation is carried out at a temperature of from 35 to 70° C. and at a hydrogen pressure of from 25 to 50 kg/cm$^2$ for a period of from about 5 to 30 hours.

6. A process as claimed in claim 1, wherein the hydrogenation is carried out in an amphiprotic solvent.

7. A process as claimed in claim 6, wherein the solvent is ethanol.

8. A process as claimed in claim 6, wherein the solvent is used in an amount of from 2 to 10 times the weight of the compound of formula (II).

9. A process as claimed in claim 8, wherein the solvent is used in an amount of from 3 to 5 times the weight of the compound of formula (II).

10. A process as claimed in claim 1, wherein said ruthenium-optically active phosphine complex is represented by formula (VI):

$$Ru(R^1\text{---}BINAP)(OCR^2)_2 \quad \text{with } C=O \quad (VI)$$

wherein R$^1$—BINAP is a tertiary phosphine represented by formula (IV):

(IV)

[Structure of R$^1$-BINAP showing binaphthyl with two P atoms each bonded to two R$^1$-substituted phenyl groups]

wherein R$^1$ represents a hydrogen atom, a methyl group or a t-butyl group; and wherein R$^2$ represents a lower alkyl group or a trifluoromethyl group.

11. A process as claimed in claim 10, wherein R$^2$ represents a lower alkyl group.

12. A process as claimed in claim 10, wherein R$^2$ represents a trifluoromethyl group.

13. A process as claimed in claim 1, wherein said ruthenium-optically active phosphine complex is represented by formula (VII):

$$[Ru(R^1\text{---}BINAP)MCl_k]_l X_m^1 \quad (VII)$$

wherein R$^1$—BINAP is a tertiary phosphine represented by formula (IV):

(IV)

[Structure of R$^1$-BINAP showing binaphthyl with two P atoms each bonded to two R$^1$-substituted phenyl groups]

wherein R$^1$ represents a hydrogen atom, a methyl group or a t-butyl group; and wherein M is Zn, Al, Ti or Sn; and X$^1$ is N(C$_2$H$_5$)$_3$ or CH$_3$CO$_2$; and in the case that X$^1$ is N(C$_2$H$_5$)$_3$, l is 2 and m is 1; and when M is Zn, then k is 4; when M is Al, then k is 5; when M is Ti or Sn, then k is 6; and in the case that X$^1$ is CH$_3$CO$_2$, l and m is 2; and when M is Zn, then k is 2, when M is Al, then k is 3; and when M is Ti or Sn, then k is 4.

14. A process as claimed in claim 13, wherein X$^1$ represents N(C$_2$H$_5$)$_3$.

15. A process as claimed in claim 13, wherein X$^1$ represents CH$_3$CO$_2$.

16. A process as claimed in claim 13, wherein M represents Zn.

17. A process as claimed in claim 13, wherein M represents Al.

18. A process as claimed in claim 13, wherein M represents Ti or Sn.

19. A process as claimed in claim 1, wherein the steric configuration of the optically active carnitine ester of formula (I) is controlled so that S-compounds are obtained by using (R)-(+)-BINAP.

20. A process as claimed in claim 1, wherein the steric configuration of the optically active carnitine ester of formula (I) is controlled so that R-compounds are obtained by using (S)-(−)-BINAP.

21. A process as claimed in claim 1, wherein the ruthenium-optically active phosphine complex is Ru((−)-BINAP) [OC(=O)CH$_3$]$_2$.

22. A process as claimed in claim 1, wherein R represents a lower alkyl group having two to four carbon atoms.

23. A process as claimed in claim 6, wherein the solvent is isopropanol.

24. A process as claimed in claim 1, wherein said ruthenium-optically active phosphine complex is used in an amount of from 1/50 to 1/5,000 mole per mole of the compound of formula (II), the hydrogenation is carried out at a temperature of from 15 to 100° C. and at a hydrogen pressure of from 10 to 150 kg/cm$^2$ for a period of from about 2 to 40 hours, in am amphiprotic solvent and wherein the amphiprotic solvent is used in an amount of from 2 to 10 times the weight of the compound of formula (II).

* * * * *